United States Patent [19]

Marshall

[11] 3,972,934

[45] Aug. 3, 1976

[54] 3-SUBSTITUTED PHENYLALKYL AMINES

[75] Inventor: Winston S. Marshall, Indianapolis, Ind.

[73] Assignee: Eli Lilly and Company, Indianapolis, Ind.

[22] Filed: Mar. 10, 1971

[21] Appl. No.: 122,999

Related U.S. Application Data

[63] Continuation-in-part of Ser. No. 828,756, May 28, 1969, Pat. No. 3,600,437, which is a continuation-in-part of Ser. Nos. 823,477, May 9, 1969, abandoned, and Ser. No. 752,801, Aug. 15, 1968, abandoned.

[52] U.S. Cl. ............ 260/570.8 R; 260/308 D; 260/465 F; 260/465 R; 260/471 A; 260/482 C; 260/488 CD; 260/500.5 H; 260/501.18; 260/501.19; 260/520 R; 260/544 D; 260/559 D; 260/570.9; 260/612 R; 424/316; 424/330
[51] Int. Cl.$^2$.......................................... C07C 87/28
[58] Field of Search ............... 260/570.8 R, 501.18, 260/501.19

[56] References Cited
UNITED STATES PATENTS
3,532,712   10/1970   Biel et al...................... 260/570.8 X

OTHER PUBLICATIONS

Ito, "Chemical Abstracts", vol. 52, pp. 9006–9007 (1958).

*Primary Examiner*—Robert V. Hines
*Attorney, Agent, or Firm*—Kathleen S. Page; Everet F. Smith

[57] ABSTRACT

Novel 3-phenoxyphenylalkyl amines and the amides, alcohols, tetrazoles, and carbamates related thereto as well as novel intermediates useful in the preparation of such compounds. The compounds of this invention are useful as anti-inflammatory, analgesic, and antipyretic agents.

16 Claims, No Drawings

3-SUBSTITUTED PHENYLALKYL AMINES

CROSS REFERENCES TO RELATED APPLICATIONS

This application is a continuation-in-part of my application Ser. No. 828,756, filed May 28, 1969, and now U.S. Pat. No. 3,600,437 which application is a continuation-in-part of my prior applications Ser. No. 823,477, filed May 9, 1969 and Ser. No. 752,801, filed Aug. 15, 1968 both now abandoned.

BACKGROUND OF THE INVENTION

This invention relates to novel 3-phenoxyphenyl alkylamines, their pharmaceutically acceptable acid addition salts, and the corresponding amides, alcohols, tetrazoles, and carbamates having anti-inflammatory activity and mild, aspirin-like, analgesic and antipyretic activity.

A number of humans and animals are known to suffer from various rheumatic conditions involving inflammation, swelling, tenderness, decreased mobility, pain, and fever. While there are a number of presently available anti-inflammatory agents which have been found to be effective in the symptomatic treatment of conditions such as rheumatoid arthritis, rheumatoid spondylitis, degenerative joint disease (osteoarthritis) of the hip, such agents have a number of undesirable side effects. One of the most frequently occurring side effects of the presently accepted nonsteroidal anti-inflammatory agents is gastric irritation, ulceration, and exacerbation of existing ulcers. Thus, the search for improved anti-inflammatory agents continues.

The present invention provides novel compounds which are excellent anti-inflammatory agents, and which, in addition to their anti-inflammatory activity, exhibit mild, aspirin-like analgesic and anti-pyretic activity. Since they are not acidic in nature, they are expected to be free of the gastro-intestinal irritating and ulcerating effects found in most non-steroidal anti-inflammatory agents.

SUMMARY

This invention relates to novel 2-(3-phenoxyphenyl)-alkylamines, their pharmaceutically acceptable acid addition salts, and the amides, alcohols, tetrazoles, and carbamates related thereto, to novel pharmaceutical compositions useful in the treatment of inflammation, pain, and fever in humans and animals, and to intermediates useful in the preparation of such compounds. Some of the compounds of this invention also enhance the analgesic activity of a number of analgesic agents.

It is a primary object of this invention to provide novel 3-phenoxyphenyl alkylamines and the amides, alcohols, tetrazoles, and carbamates related thereto.

Still a further object is to provide therapeutic compositions for the relief of inflammation, and the accompanying pain, swelling, fever, and the like in man and animals.

A further object is to provide methods for treating inflammation in man and animals.

Further objects will become apparent to those skilled in the art from the following description and claims.

DETAILED DESCRIPTION OF PREFERRED EMBODIMENTS

The novel 3-phenoxyphenyl alkylamines, their pharmaceutically acceptable acid addition salts and the corresponding amides, alcohols, carbamates, and tetrazoles of this invention are represented by general formula I:

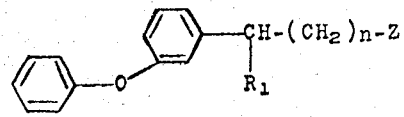

wherein
$R_1$ is hydrogen, $C_1$–$C_5$ alkyl, $C_2$–$C_5$ alkenyl, or $C_2$–$C_5$ alkynyl;
$n$ is an integer from 0 to 3; and
$Z$ is (a) 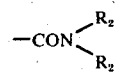

wherein each $R_2$ is the same or different and is hydrogen, hydroxy, $C_1$–$C_5$ alkyl, or —CH$_2$—COOR$_3$; where $R_3$ is hydrogen, $C_1$ to $C_5$ alkyl, or a pharmaceutically acceptable cation, (b) —CH$_2$OR$_4$, $R_4$ being hydrogen, acetyl, propionyl, carbamyl, N-methylcarbamyl, or N,N-dimethylcarbamyl;

(c) 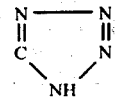

, or
(d) when $n = 1$–$3$,

wherein each $R_5$ is the same or different, and is hydrogen, $C_1$–$C_5$ alkyl, $C_2$–$C_6$ alkenyl, cyclopropyl, or cyclopropylmethyl, allyl, 3-methyl-2-butenyl, or phenethyl;
and the pharmaceutically acceptable acid addition salts thereof.

The term "acid addition salts" refers to salts prepared by reacting the free amine with an organic or inorganic acid. Representative salts include the hydrochloride, hydrobromide, sulfate, bisulfate, acetate, valerate, oleate, laurate, borate, benzoate, lactate, phosphate, tosylate, citrate, maleate, fumarate succinate, tartrate, napsylate (salt of 2-naphthalenesulfonic acid) and the like.

"$C_1$–$C_5$ alkyl" refers to both straight and branched chain alkyls including methyl, ethyl, n-propyl, iso-propyl, n-butyl, sec-butyl, tert-butyl, iso-butyl, n-amyl, iso-amyl, neo-pentyl, and the like.

"$C_2$–$C_5$ alkenyl" refers to the $C_2$–$C_5$ alkyl groups, as defined above, from which a hydrogen atom has been removed from each of two adjacent carbon atoms to produce ethylenic unsaturation; e.g., vinyl, allyl, methallyl, 1-pentenyl, and the like.

"$C_1$–$C_5$ alkynyl" refers to the $C_2$–$C_5$ alkyl groups as defined above, from which two hydrogen atoms have been removed from each of two adjacent carbon atoms to produce acetylenic unsaturation; e.g., ethynyl, propargyl, 2-butynyl, 1-pentynyl, and the like.

Compounds represented by general formula I are excellent anti-inflammatory agents, many of them having an $ED_{50}$ of from 1–10 mg./kg. in the erythema blocking assay. All of the compounds of this invention are useful in the treatment of inflammatory diseases in mammals. In addition to their anti-inflammatory activity, the compounds exhibit mild analgesic and antipyretic activity. Therapeutic compositions comprising, as their active ingredient(s), one or more compounds of general formula I in association with a pharmaceutically acceptable diluent or carrier, are also provided by this invention. The compounds are generally administered to mammals in dosages of from 0.5–50 mg./kg. of body weight daily, either in single or divided doses over a period of 24 hours.

It is to be understood that both the $d$ and $l$ isomers of the $\alpha$-alkyl compounds of this invention are contemplated within the scope of the invention. Thus, for example, the $\alpha$-alkylamine can be resolved into their $d$ and $l$ isomers by methods well known in the art.

Some of the compounds of this invention, particularly those wherein $n$ is 1, $R_1$ is methyl, and Z is $-NH_2$ or a salt thereof, have surprisingly been found to enhance the level of analgesia obtained with certain analgesic agents such as the esters of $d$-1,2-diphenyl-2-hydroxy-3-methyl 4(substituted amino)butanes, particularly $\alpha$-d-propoxyphene (identified chemically as $\alpha$-d-1,2-diphenyl-2-propionoxy-3-methyl-4-dimethylaminobutane) when co-administered therewith.

Enhancement of analgesia is effected when about one part by weight of a compound of this invention is administered substantially simultaneously, that is, co-administrated, or administered from 1 hour before to 1 hour after the administration of from 0.005 to 20 parts by weight of the analgesic agent. Generally speaking, in order to obtain a greater level of analgesia, from 0.5 to 50 mg./kg. of a compound of this invention is administered with the usual therapeutic dosage of the analgesic agent.

Representative compounds of the present invention include the following:
2-(3-Phenoxyphenyl)propanol
2-(3-Phenoxyphenyl)propionamide
2-(3-Phenoxyphenyl)ethylcarbamate
N-Methyl-2-(3-phenoxyphenyl)propionamide
N-Methyl-2-(3-phenoxyphenyl)propylcarbamate
N,N-Dimethyl-2-(3-phenoxyphenyl)propionamide
N,N-Dimethyl-2-(3-phenoxyphenyl)-n-pentyl carbamate
N-Cyclopropylmethyl-2-(3-phenoxyphenyl)propionamide
2-(3-Phenoxyphenyl)ethylamine
N-Cyclopropyl-2-(3-phenoxyphenyl)butylamine maleate
2-(3-Phenoxyphenyl)propionohydroxamic acid
N-Cyclopropylmethyl-2-(3-phenoxyphenyl)propylamine hydrochloride
N-Methyl-2-(3-phenoxyphenyl)propylamine sulfate
N,N-Dimethyl-2-(3-phenoxyphenyl)propylamine hydrochloride
2-(3-Phenoxyphenyl)propylamine hydrochloride
2-(3-Phenoxyphenyl)butylamine sulfate
3-(3-Phenoxyphenyl)butanol
3-(3-Phenoxyphenyl)butyl acetate
2-(3-Phenoxyphenyl)propyl propionate
5-($\alpha$-Methyl-3-phenoxybenzyl)-1H-tetrazole
5-(3-phenoxyphenyl)-1H-tetrazole
4-(3-Phenoxyphenyl)valeramide The compounds of this invention can be prepared by methods which are well known for the preparation of arylalkylamines, arylalkanoic acid amides, arylalkanols and derivatives thereof. While various routes can be employed in obtaining the compounds of this invention, a number of the preferred reaction sequences are represented and described hereinbelow. In the following representations and discussion, $R_1$-$R_4$ are as defined in formula I, and "Ar" represents the

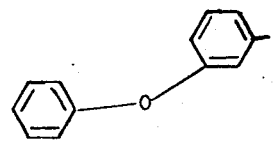

moiety of formula I.

A. Acids

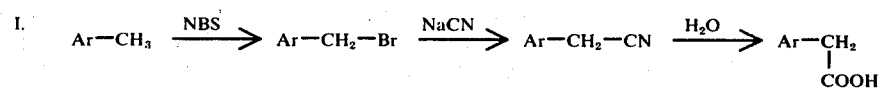

The methyl group of m-phenoxytoluene is halogenated by the action of N-bromosuccinimide, N-chlorosuccinimide, sulfurylchloride, or like halogenating agent, with a suitable catalyst, such as benzoyl peroxide or azo-bis-iso-butyronitrile, in an inert solvent such as carbon tetrachloride, or other halogenated hydrocarbon. The resulting halomethyl diphenyl ether is caused to react with sodium or potassium cyanide, advantageously in dimethyl sulfoxide solution. The nitrile thus obtained is hydrolyzed to the corresponding carboxylic acid by the action of either acidic or basic reagents by methods well known in the art.

B. $\alpha$-Alkyl Acids

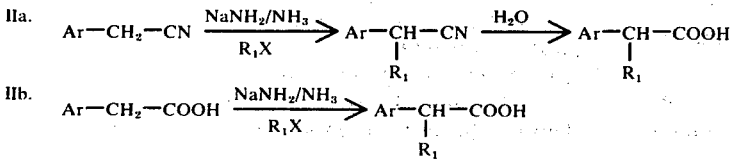

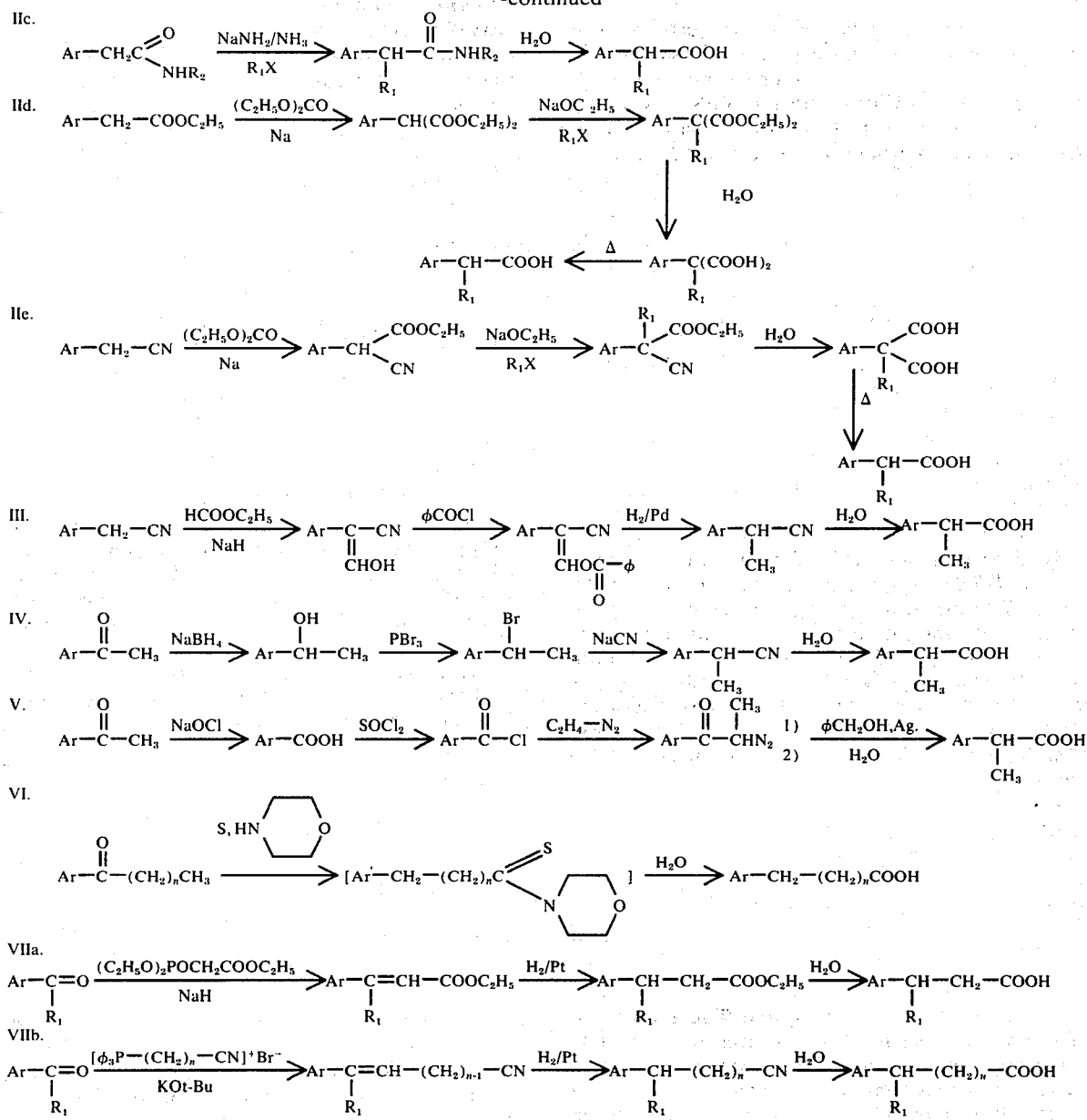

The nitrile prepared in the above illustration can be alkylated with an aliphatic halide or tosylate ($R_1X$) in liquid ammonia in the presence of sodium amide to provide an α-aliphatic substituted nitrile. The alkylated nitrile is hydrolyzed as above to yield the corresponding carboxylic acid (Sequence IIa). In a similar fashion, an arylacetic acid or arylacetamide may be alkylated α- to the carboxyl group, as illustrated in reaction sequence IIb–IIc. In the case of the arylacetamide, the resulting α-alkyl derivative can be hydrolyzed to the corresponding carboxylic acid if desired.

In another method, as illustrated in sequences IId and IIe, an arylacetate ester, such as the ethyl ester, or an arylacetonitrile can be converted to the corresponding malonic ester or cyanoacetic ester by the action of metallic sodium and diethyl carbonate. Either of these derivatives may then be alkylated. Such alkylation is usually effected by reacting the malonic ester or cyanoacetic ester with a strongly basic reagent, such as sodium ethoxide, sodium methoxide, potassium tert-butoxide, sodium hydride, and the like, thereby forming a carbanion on the α-carbon atom. Subsequent treatment of the carbanion intermediate with an alkylating agent, such as an alkyl halide or tosylate ($R_1X$) yields the corresponding α-alkyl malonic ester or cyanoacetic ester derivative. Either of these may be hydrolyzed to the corresponding α-alkylaryl malonic acid which is then decarboxylated by methods well known in the art, thus yielding the desired α-alkyl arylacetic acid.

A nitrile prepared according to reaction sequence I can optionally be methylated according to the following procedure (Sequence III): The nitrile is condensed with ethyl formate under basic conditions, for example, in the presence of sodium hydride or sodium methoxide in an inert hydrocarbon solvent such as in benzene. The resulting hydroxymethylene derivative is benzoylated by the action of either benzoic anhydride or benzoyl chloride and pyridine; and the benzoic ester is then hydrogenated in the presence of a noble metal catalyst to yield the desired α-methylarylacetonitrile, which is then hydrolyzed as above.

The desired α-methylarylacetonitrile can optionally be prepared by the following series of reactions (Sequence IV); the m-phenoxyacetophenone (prepared by the method of an Ullman Ether synthesis) is reduced either with hydrogen in the presence of a noble metal catalyst or with a metal hydride, such as lithium aluminum hydride, lithium or sodium borohydride, or the like, to the corresponding carbinol. Conversion of this carbinol to the corresponding bromide can be accomplished by treating the carbinol with phosphorus tribromide, preferably in an inert solvent such as chloroform, benzene, carbon tetrachloride, and the like. The bromide thus obtained is then reacted with sodium cyanide advantageously in a dimethyl sulfoxide solution to yield a nitrile which is hydrolyzed, as set forth above, to the desired carboxylic acid.

An alternate method of synthesizing α-alkyl -(m-phenoxyphenyl)acetic acids involves the use of the Arndt-Eistert reaction, as illustrated in sequence V, using m-phenoxy benzoic acid as the starting material.

The phenoxyphenyl alkanoic acids can also be prepared by the Willgerodt reaction (Sequence VI). In this reaction, a m-phenoxyphenyl alkyl ketone is heated with, for example, morpholine and sulfur, and the resulting thioamide hydrolyzed to yield the desired alkanoic acid derivative which can be alkylated by treatment with two equivalents of sodium amide in liquid ammonia, followed by the addition of the alkyl halide or tosylate ($R_1X$) as illustrated in sequence IIb.

The acid intermediates in which $n$ is other than O can be prepared by well-known methods with the well-known Wittig reaction as illustrated in reaction schemes VIIa and VIIb. The intermediate unsaturated esters (as in VIIa) or nitriles (as in VIIb) can be hydrogenated in the presence of a noble metal catalyst, such as platinum, and the resulting saturated esters and nitriles can be hydrolyzed, as set forth above, to the desired carboxylic acids.

C. Esters

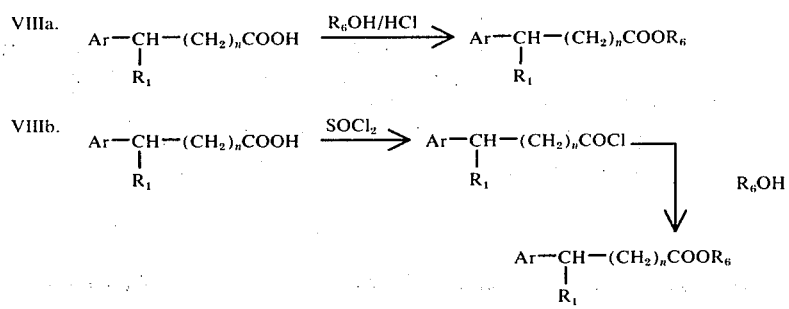

The carboxylic acid intermediates prepared by methods described in the above reaction sequences are converted to the corresponding esters by well-known methods of the prior art such as by heating the acid with an alcohol in the presence of a mineral acid (VIIIa), or by converting the acid to the corresponding acid chloride, followed by reacting said acid chloride with an alcohol, preferably in the presence of an HCl scavenger (VIIIb).

D. Amides

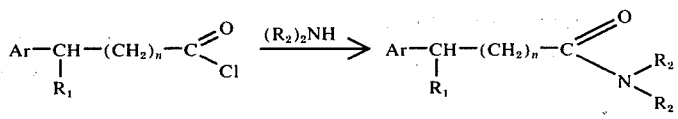

The amides of this invention are obtained by the reaction of the aforementioned acid chloride with an amine. This reaction is customarily carried out in an inert solvent such as chloroform, benzene, or carbon tetrachloride, in the presence of an acid scavenger such as pyridine, $K_2CO_3$, and the like, or in a tertiary amine solvent such as collidine, lutidine, triethylamine, and the like.

E. Alcohols

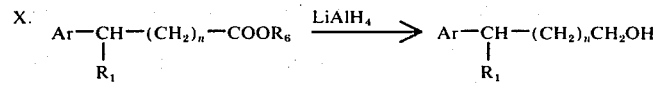

The esters whose preparation is outlined above can be reduced with a metal hydride such as, for example, lithium aluminum hydride, to the corresponding alcohol by the methods of the prior art.

F. Esters

XIa.

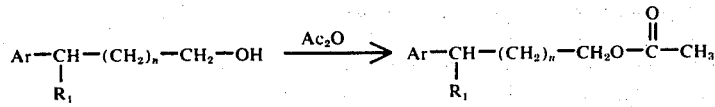

The new alcohols obtained as set forth in reaction sequence X can be converted to ester derivatives by well-known methods, such as, for example, treatment of the alcohol with an acid chloride or acid anhydride, preferably in the presence of a tertiary amine such as pyridine or triethylamine. Such a reaction using acetic anhydride, for example, yields the desired acetate ester.

G. Carbamates

XIb.

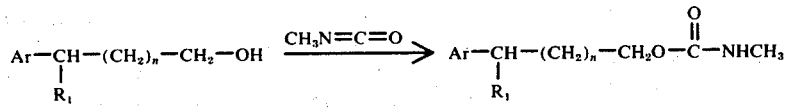

Carbamate derivatives of the alcohols obtained as in reaction sequence X can also be prepared, either by reaction of the alcohol with an iso-cyanate or by reaction of the alcohol with a carbamoyl halide, such as N,N-dimethylcarbamoyl chloride. These reactions are preferably conducted using a tertiary amine solvent, such as pyridine or triethylamine.

H. Amines

XIIa.

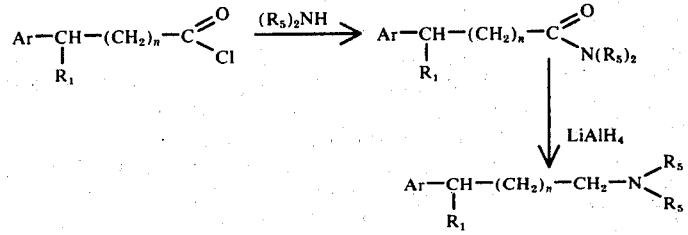
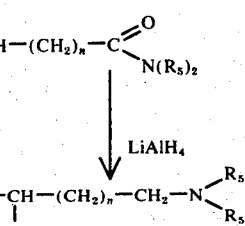

XIIb.

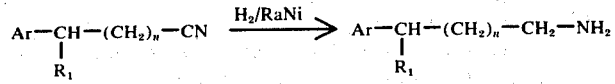

XIIc.

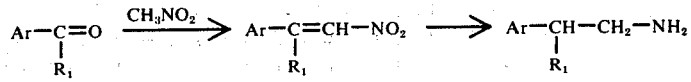

The amine derivatives of this invention can be prepared by well-known procedures, such as, for example, reduction of an amide with a metal hydride reagent such as lithium aluminum hydride (Sequence XIIa). In those cases where primary amines are desired, these can conveniently be prepared by hydrogenation of the corresponding nitriles in the presence of ammonia and an active catalyst, such as Raney nickel (Sequence XIIb).

A suitably substituted aryl alkyl ketone may optionally be condensed with nitromethane and the resulting nitro-styrene derivative can then be reduced either catalytically or with a metal hydride reagent such as lithium aluminum hydride, to yield the desired amine (Reaction Sequence XIIc).

I. Hydroxamic Acids

XIII.

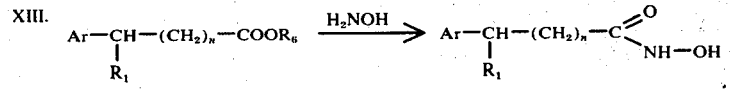

The esters prepared according to reaction sequence VIIIa and VIIIb can be converted into hydroxamic acids by treatment with hydroxylamine by well-known procedures.

J. Tetrazoles

XIV.

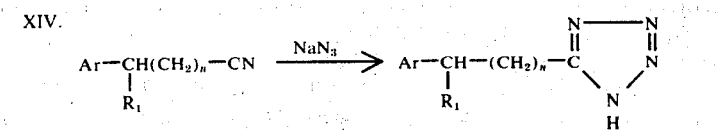

Nitriles which are prepared by the methods of sequences I, IIa, III, or IV, or by other well-known methods, can be converted to the corresponding tetrazoles by treating them with, for example, sodium azide, using dimethylformamide as the reaction solvent (in the manner described by Finnigan, W. G., Henry, R. A., and Lofquist, R., *J. Am. Chem. Soc.*, 80, 2908 (1958)). de The following examples further illustrate the present invention.

EXAMPLE 1

A. Preparation of 2-(3-phenoxyphenyl)acetic acid

To 26 ml. of morpholine were added 42.4 g. of m-phenoxyacetophenone and 9.6 g. of sulfur. The reaction mixture was refluxed with stirring for 20 hours. To the reaction mixture was then added 700 ml. of 15 percent aqueous potassium hydroxide and a small amount of ethyl alcohol. The reaction mixture was refluxed with stirring for an additional 20 hours. About 200 ml. of the solvent was distilled out. The remaining reaction mixture was filtered while hot, partially cooled with ice, and acidified with concentrated hydrochloric acid, whereupon an oily precipitate formed and then crystallized. The crystalline precipitate was filtered, washed several times with water, and dried to yield 45.9 g. of crude product as a yellow-orange solid. The crude product was suspended in boiling hexane, and ethyl acetate was added until the product went into solution. The solution was then treated with carbon, filtered and cooled, to yield 22.7 g. of white flakes of 2-(3-phenoxyphenyl)acetic acid, m.p., 84°–86°C.; pK'a = 6.9.

Analysis, Calc. for $C_{14}H_{12}O_3$: C, 73.66; H, 5.30. Found: C, 73.85; H, 5.35.

B. Methyl 2-(3-phenoxyphenyl)acetate 2-(3-Phenoxyphenyl)acetic acid is dissolved in chloroform, stirred, and thionyl chloride in chloroform is added slowly. The reaction mixture is refluxed gently with stirring for about 3 hours, and then evaporated to dryness to yield the corresponding acid chloride. The acid chloride is taken up in chloroform and the resulting solution added dropwise with stirring to an excess of cold methyl alcohol. The reaction mixture is cooled to below 10°C., and then allowed to warm to room temperature. The solvent is stripped off on a rotary evaporator and the residue distilled to yield methyl 2-(3-phenoxyphenyl)acetate. This compound can be used as an intermediate in the preparation of the new alcohol compounds of this invention.

EXAMPLE 2

Preparation of 2-(3-Phenoxyphenyl)propionic acid

A. 3-Phenoxyacetophenone.

A mixture consisting of 908 g. (6.68 moles) of m-hydroxyacetophenone, 4500 g. (28.6 moles) of bromobenzene, 996 g. (7.2 moles) of anhydrous potassium carbonate, and 300 g. of copper bronze was heated under reflux with stirring until water evolution was complete, using a Dean-Stark water separator. The mixture was then stirred and refluxed for 24 hours. After cooling to room temperature, the reaction was diluted with an equal volume of $CHCl_3$ and filtered. The filtrate was washed with 5 percent HCl, then with 5 percent NaOH, with water, dried over $Na_2SO_4$, and evaporated in vacuo. The residual oil was distilled through a 15 cm. Vigreux column, yielding 918 g. of 3-phenoxyacetophenone, b.p., 120°–121°C. (0.09 mm.), $n_D^{25} = 1.5868$.

Analysis, Calc. for $C_{14}H_{12}O_2$: C, 79.22; H, 5.70. Found: C, 79.39; H, 5.79.

B. α-Methyl-3-phenoxybenzyl alcohol

A stirred solution of 700 g. of m-phenoxyacetophenone in 3000 ml. anhydrous methanol was cooled to 0° in an ice-acetone bath. Sodium borohydride, 136 g. (3.6 moles) was added to this solution in small portions at such a rate that the temperature never rose above 10°C. After borohydride addition was complete, the reaction mixture was allowed to warm to room temperature and stirred for 18 hours. It was then stirred and refluxed for 8 hours. About 400 ml. of methanol was distilled out and the remaining solution was evaporated to about one-third its original volume in vacuo and poured into ice water. This mixture was extracted twice with ether, acidified with 6NHCl, and again extracted with ether. The ether extracts were combined, washed with saturated NaCl solution, dried over anhydrous sodium sulfate, and evaporated in vacuo. The residual oil was distilled through a 15 cm. Vigreux column, yielding 666 g. of α-methyl-3-phenoxybenzyl alcohol, b.p., 132°–134°C. (0.35 mm.). $n_D^{25} = 1.5809$.

Analysis, Calc. for $C_{14}H_{14}O_2$: C, 78.48; H, 6.59. Found: C, 78.75; H, 6.31.

C. α-Methyl-3-phenoxybenzyl bromide.

A stirred solution of 1357 g. of α-methyl-3-phenoxybenzyl alcohol in 5000 ml. anhydrous $CCl_4$ (predried over molecular sieve) was cooled to 0°C. To this was added 1760 g. $PBr_3$, stirring and cooling being maintained at such a rate that the temperature remained at 0°–5°C. during the addition. The reaction mixture was then allowed to warm to room temperature and was stirred at room temperature overnight (ca. 12 hours). The reaction mixture was then poured into ice water and the organic phase separated. The aqueous phase was extracted with $CCl_4$ and the combined extracts were washed three times with water, dried over anhydrous sodium sulfate, and evaporated to dryness in vacuo to yield 1702 g. of α-methyl-3-phenoxybenzyl bromide as a heavy viscous oil, $n_D^{25} = 1.5993$;

Analysis, Calc. for $C_{14}H_{13}BrO$: C, 60.44; H, 4.71; Br, 28.73. Found: C, 60.62; H, 4.89; Br, 28.47.

D. 2-(3-Phenoxyphenyl)propionitrile

A well-stirred suspension of 316 g. of 98 percent sodium cyanide in 5000 ml. of anhydrous dimethyl sulfoxide (previously dried over molecular sieve) was warmed to 55°–60°C. and maintained at this temperature while 1702 g. of α-methyl-3-phenoxybenzyl bromide was slowly added. After the bromide addition was completed, the temperature was raised to 75°C., and the mixture stirred at this temperature for 1.5 hours. The mixture was then allowed to cool to room temperature, and was stirred overnight at room temperature and then poured into ice water. The resulting aqueous suspension was extracted twice with ethyl acetate, and then with ether. The organic extract was washed twice with a sodium chloride solution, once with water, and dried over anhydrous sodium sulfate. Evaporation of the solvent in vacuo left an oily residue which was distilled through a 15 cm. Vigreux column to yield 1136 g. of 2-(3-phenoxyphenyl)propionitrile, b.p., 141°–148°C. (0.1 mm.), $n_D^{25} = 1.5678$.

Analysis, Calc. for $C_{15}H_{13}NO$: C, 80.69; H, 5.87; N, 6.27. Found: C, 80.89; H, 6.10; N, 6.14.

E. 2-(3-Phenoxyphenyl)propionic Acid

A mixture of 223 g. of 2-(3-phenoxyphenyl)propionitrile and 400 g. of sodium hydroxide in 1600 ml. of 50 percent ethanol was refluxed with stirring for 72 hours. After cooling to room temperature, the reaction mixture was poured into ice water. The resulting solution was washed with ether, acidified with concentrated HCl, and extracted with ether. The ether extract was washed with water, dried over anhydrous sodium sulfate, and evaporated to dryness in vacuo. The residual oil was distilled to yield 203.5 g. (84 percent) of 2-(3-phenoxyphenyl)propionic acid as a viscous oil; b.p., 168°–171°C. (0.11 mm.), $n_D{}^{25}$ = 1.5742, pK'a = 7.3.

Analysis, Calc. for $C_{15}H_{14}O_3$: C, 74.36; H, 5.83. Found: C, 74.48; H, 6.05.

EXAMPLE 3

5-(α-Methyl-3-phenoxybenzyl)-1H-tetrazole

A well-stirred mixture of 10 g. of 2-(3-phenoxyphenyl)propionitrile, prepared according to the method of example 2D, 3.9 g. of sodium azide, 3.2 g. of ammonium chloride, a few milligrams of lithium chloride and 200 ml. of dry dimethylformamide was heated to 125°C. for about 18 hours. Afer cooling, the dimethylformamide was partially evaporated in vacuo and the remaining reaction mixture was poured into water. After adjusting this aqueous mixture to pH4 with dilute HCl, the product precipitated as an oil. After the aqueous solution was removed by decantation, the oil solidified. It was recrystallized from a mixture of ethyl acetate and n-hexane to yield 4.7 g. of 5-(α-methyl-3-phenoxybenzyl)-1H-tetrazole, m.p., 92°–95°C., pK'a 5.8.

Analysis, Calc. for $C_{15}H_{14}N_4O$: C, 67.65; H, 5.30; N, 21.04. Found: C, 67.41; H, 5.33; N, 21.05.

EXAMPLE 4

2-(3-Phenoxyphenyl)propionamide

A solution of 0.5 M of 2-(3-phenoxyphenyl)propionyl chloride in 300 ml. of dry ethyl ether was added dropwise to 2 liters of liquid ammonia with stirring. After addition was complete, the reaction was stirred for one hour, and 500 ml. of diethyl ether were added. The reaction was stirred overnight, whereby the excess ammonia was evaporated. Dilute hydrochloric acid was added to the reaction. The ether layer was separated, washed with sodium hydroxide, water, and dried over sodium sulfate. Evaporation of the ether in vacuo left a gummy residue which crystallized after trituration with cold hexane. Recrystallization from ethyl acetate and hexane yielded 76.2 g. of 2-(3-phenoxyphenyl)propionamide, m.p., 67°–69°C.

Analysis, Calc. for $C_{15}H_{15}NO_2$: C, 74.66; H, 6.27; N, 5.81. Found: C, 74.01; H, 6.30; N, 6.15.

EXAMPLE 5

N,N-Dimethyl-2-(3-phenoxyphenyl)propionamide

To 400 ml. of dry chloroform were added 72.6 g. of 2-(3-phenoxyphenyl)propionic acid prepared according to the method of Example 2E, and 36.9 g. of thionyl chloride. The reaction mixture was refluxed with stirring for about 3 hours. The chloroform was then evaporated and the residue azeotroped twice with benzene. The residue was dissolved in ethyl ether and added, with stirring and cooling, to a solution of 45 g. of dimethylamine in ethyl ether. The temperature was maintained at approximately 0°C. or below during the addition. The reaction mixture was allowed to warm to room temperature, refluxed gently for 1.5 hours, poured into ice and water, acidified, and the ethyl ether layer separated. The aqueous layer was extracted with ethyl ether. The ether extracts were combined, washed with water, dried over sodium sulfate and evaporated to white solid. The solid was dissolved in boiling hexane and allowed to cool slowly to room temperature to yield 67.6 g. of N,N-dimethyl-2-(3-phenoxyphenyl)-propionamide, m.p., 73.5°–76°C., Analysis, Calc. for $C_{17}H_{19}NO_2$: C, 75.80; H, 7.11; N, 5.20. Found: C, 75.93; H, 6.90; N, 5.27.

EXAMPLE 6

N-Cyclopropylmethyl-2-(3-phenoxyphenyl)pripionamide

To 350 ml. of chloroform were added 60.5 g. of 2-(3-phenoxyphenyl)propionic acid and 30.4 g. of thionyl chloride. The reaction mixture was refluxed with stirring overnight, evaporated, and the residue azeotroped three times with benzene. The resulting oily acid chloride was taken up in chloroform. Forty grams of aminomethylcyclopropane hydrochloride were dissolved in a small amount of water, made basic with 5N sodium hydroxide, and extracted with chloroform. The aqueous layer was saturated with sodium chloride and again extracted with chloroform. The chloroform extracts were combined and dried over sodium carbonate and sodium sulfate. The extracts were filtered, and 50 ml. of triethylamine added thereto. The mixture was cooled in an ice-acetone bath. To this was added dropwise the chloroform solution of the acid chloride. Cooling and stirring were maintained during the addition.

The reaction mixture was allowed to warm to room temperature, stirred for 30 minutes, warmed to the reflux point, allowed to cool to room temperature, and stirred overnight. The solution was then partially evaporated and poured into an ice-water mixture. The chloroform layer was washed with dilute hydrochloric acid, dried over sodium sulfate, and evaporated to an oily residue. The residue was covered with hexane and scratched, whereupon a crystalline solid formed. The crystalline solid was taken up in boiling ethyl acetate, and hexane was added to turbidity. The solution was allowed to cool to yield 50.6 g. of crystalline N-cyclopropylmethyl-2-(3-phenoxyphenyl)propionamide, m.p., 94.5°–96°C.

Analysis, Calc. for $C_{19}H_{21}NO_2$: C, 77.26; H, 7.17; N, 4.74. Found: C, 77.14; H, 7.17; N, 4.71.

EXAMPLES 7–17

The following compounds were prepared according to the method of Example 6, using appropriate starting materials.

N-Methyl-2-(3-phenoxyphenyl)butyramide, m.p., 84°–86°C.

Analysis, Calc. for $C_{17}H_{19}NO_2$: C, 75.81; H, 7.11; N, 5.20. Found: C, 75.60; H, 7.11; N, 5.00.

N-Methyl-2-(3-phenoxyphenyl)propionamide, m.p., 57°–58°C.

Analysis, Calc. for $C_{16}H_{17}NO_2$: C, 75.27; H, 6.71; N, 5.49. Found: C, 75.51; H, 6.86; N, 5.61.

N-Cyclopropyl-2-(3-phenoxyphenyl)propionamide, m.p., 65°–67°C.

Analysis, Calc. for $C_{18}H_{19}NO_2$: C, 76.84; H, 6.81; N, 4.98. Found: C, 77.06; H, 6.99; N, 4.94.

N-Methyl-(3-phenoxyphenyl)acetamide, m.p., 64°–68°C., which gave a satisfactory Nmr spectrum and which was used without purification.

N,N-Dimethyl-3-phenoxyphenylacetamide, an oil which have a satisfactory Nmr spectrum and which was used without purification.

Ethyl-[N-cyclopropyl-N-(2-[3-phenoxyphenyl]-propyl)]carbamate, which gave a satisfactory Nmr spectrum and which was used without purification.

N-Methyl-N-(2-[3-phenoxyphenyl]propyl)cyclopropane carboxamide, which gave a satisfactory Nmr spectrum.

Analysis, Calc. for $C_{20}H_{25}NO_2$: C, 77.64; H, 7.49; N, 4.53; O, 10.34. Found: C, 77.90; H, 7.71; N, 4.40; O, 10.58.

Ethyl-N-(2-phenethyl)-N-[2-(3-phenoxyphenyl)-propyl]carbamate, which gave a satisfactory Nmr spectrum.

Analysis, Calc. for $C_{26}H_{29}NO_3$: C, 77.39; H, 7.24; N, 3.47; O, 11.90. Found: C, 77.17; H, 7.46; N, 3.65; O, 12.04.

N-Allyl-2-(3-phenoxyphenyl)propionamide, which gave a satisfactory Nmr spectrum.

Analysis, Calc. for $C_{18}H_{19}NO_2$: C, 76.84; H, 6.81; N, 4.98. Found: C, 76.85; H, 7.03; N, 4.93.

N-2-(phenyl)ethyl-2-(3-phenoxyphenyl)propionamide, m.p., 55°–56°C.; which gave a satisfactory Nmr spectrum and which was used without further purification.

3-(3-Phenoxyphenyl)butyramide, m.p., 50°–53°C.

Analysis, Calc. for $C_{16}H_{17}NO_2$: C, 75.27; H, 6.71; N, 5.49. Found: C, 75.51; H, 6.71; N, 5.27.

EXAMPLE 18

N,N-Dimethyl-2-(3-phenoxyphenyl)propylamine hydrochloride

To a flame dried flask were added, under nitrogen, 6.08 g. of lithium aluminum hydride and 500 ml. of ethyl ether. The mixture was stirred at room temperature for approximately 30 minutes. To the mixture was added dropwise 67.3 g. of N,N-dimethyl-2-(3-phenoxyphenyl)propionamide (prepared according to the method of Example 5) dissolved in 800 ml. of ethyl ether. The reaction mixture was refluxed with stirring overnight. To the reaction mixture was then added 4.65 ml. of water, 3.5 ml. of 20 percent sodium hydroxide, and 16.5 ml. of water. The reaction mixture was then poured onto ice, additional sodium hydroxide was added, and the reaction was extracted with ethyl ether. The ether layer was washed with water and extracted with dilute hydrochloric acid. The acid extract was then washed with ethyl ether, basified with sodium hydroxide, and extracted twice with ethyl ether. The ether extracts were washed with water, dried over sodium sulfate, and evaporated to an oil. The oil was distilled to yield 39.2 g. of N,N-dimethyl-2-(3-phenoxyphenyl)propylamine, b.p., 114°–120°C./0.1 mm., m.w. 255.

Analysis, Calc for $C_{17}H_{21}NO$: C, 79.96; H, 8.29; N, 5.49. Found: C, 79.76; H, 8.06; N, 5.38.

Thirty-four grams of the above amine were dissolved in approximately 800 ml. of dry ethyl ether, and hydrogen chloride gas was passed into the solution until saturated. The resulting white solid precipitate was filtered, washed with ethyl ether, partially dried, and recrystallized from boiling ethyl alcohol to yield 34.3 g. of N,N-dimethyl-2-(3-phenoxyphenyl)propylamine hydrochloride, m.p., 215°–217°C.

Analysis, Calc. for $C_{17}H_{21}NO \cdot HCl$: C, 69.96; H, 7.60; N, 4.80. Found: C, 69.68; H, 7.40; N, 4.90.

EXAMPLES 19–31

The following compounds were prepared according to the method of Example 18, from the corresponding amide using appropriate starting materials.

N-Methyl-2-(3-phenoxyphenyl)butylamine hydrochloride, m.p., 124°–126°C.

Analysis, Calc. for $C_{17}H_{21}NO \cdot HCl$: C, 69.96; H, 7.60; N, 4.80. Found: C, 69.83; H, 7.80; N, 4.87.

N-Methyl-2-(3-phenoxyphenyl)propylamine hydrochloride, m.p., 160°–162°C.

Analysis, Calc. for $C_{16}H_{19}NO \cdot HCl$: C, 69.17; H, 7.25; N, 5.04. Found: C, 69.21; H, 7.02; N, 5.30.

N-Cyclopropylmethyl-2-(3-phenoxyphenyl)propylamine hydrochloride, m.p., 115°–117°C.

Analysis, Calc. for $C_{19}H_{23}NO \cdot HCl$: C, 71.79; H, 7.61; N, 4.40. Found: C, 71.96; H, 7.46; N, 4.39.

N-Cyclopropyl-2-(3-phenoxyphenyl)propylamine hydrochloride, m.p., 129°–131°C., pK'a 7.9.

Analysis, Calc. for $C_{18}H_{21}NO \cdot HCl$: C, 71.15; H, 7.30; N, 4.61. Found: C, 71.23; H, 7.48; N, 4.61.

N-Methyl-2-(3-phenoxyphenyl)ethylamine hydrochloride, m.p., 139°–141°C., pK'a 9.7.

Analysis, Calc. for $C_{15}H_{17}NO \cdot HCl$: C, 68.30; H, 6.88; N, 5.31. Found: C, 68.21; H, 6.75; N, 5.13.

N,N-Dimethyl-2-(3-phenoxyphenyl)ethylamine hydrochloride, m.p., 163°–165°C., pK'a 8.5.

Analysis, Calc. for $C_{16}H_{19}NO \cdot HCl$: C, 69.18; H, 7.26; N, 5.04; O, 5.76. Found: C, 69.38; H, 7.45; N, 5.07; O, 5.59.

N-Methyl-N-cyclopropyl-2-(3-phenoxyphenyl)-propylamine hydrochloride, m.p., 129°–130°C., pK'a 6.9.

Analysis, Calc. for $C_{19}H_{23}NO \cdot HCl$: C, 71.80; H, 7.61; N, 4.41. Found: C, 71.53; H, 7.84; N, 4.58.

N-Methyl-N-cyclopropylmethyl-2-(3-phenoxyphenyl)propylamine hydrochloride, m.p., 90°–92°C, pK'a 8.3.

Analysis, Calc. for $C_{20}H_{25}NO \cdot HCl$: C, 72.38; H, 7.90; N, 4.22; O, 4.82. Found: C, 72.33; H, 7.90; N, 4.41; O, 5.09.

N-Methyl-N-(2-phenylethyl)-2-(3-phenoxyphenyl)-propylamine hydrochloride, m.p., 137°–138°C, pK'a 7.7.

Analysis, Calc. for $C_{24}H_{27}NO \cdot HCl$: C, 75.46; H, 7.39; N, 3.67. Found: C, 75.23; H, 7.58; N, 3.56.

N-Allyl-2-(3-phenoxyphenyl)propylamine hydrochloride, m.p., 118°–120°C., pK'a 8.5.

Analysis, Calc. for $C_{18}H_{21}NO$: C, 71.16; H, 7.30; N, 4.61. Found: C, 71.13; H, 7.50; N, 4.54.

N-(2-Phenylethyl)-2-(3-phenoxyphenyl)propylamine hydrochloride, m.p. 120°–124°C.

Analysis, Calc. for $C_{23}H_{25}NO \cdot HCl$: C, 75.08; H, 7.12; N, 3.81. Found: C, 75.11; H, 7.30; N, 3.64.

N-Methyl-3-(3-phenoxyphenyl)butylamine hydrochloride, m.p., 124°–126°C., pK'a 10.0.

Analysis, Calc. for $C_{17}H_{21}NO \cdot HCl$: C, 69.96; H, 7.60; N, 4.80. Found: C, 69.83; H, 7.80; N, 4.87.

3-(3-Phenoxyphenyl)butylamine hydrochloride, m.p., 133°–135°C., pK'a 10.0.

Analysis, Calc. for $C_{16}H_{19}NO \cdot HCl$: C, 69.17; H, 7.26; N, 5.04. Found: C, 69.36; H, 7.47; N, 5.06.

EXAMPLE 32

N-Methyl-N-(3-methylbut-2-enyl)-2-(3-phenoxyphenyl)propylamine hydrochloride A mixture of 23.9 g. of N-Methyl-2-(3-phenoxyphenyl)propylamine, prepared according to the method of Example 20, and 13.8 g. of potassium carbonate in benzene was treated with 20.8 g. of 1-chloro-3-methyl-2-butene. The reaction mixture was refluxed with mechanical stirring for about 60 hours. After cooling to room temperature, the reaction was washed with water and extracted with dilute hydrochloric acid. The acidic extract was basified with sodium hydroxide solution and extracted with ether. The ether extract was washed twice with water and dried over sodium sulfate. Dry hydrogen chloride gas was passed into the ethereal solution and the resulting precipitated hydrochloride salt was filtered and recrystallized from an alcohol-ether mixture to yield 11.5 g. of the titled product, m.p. 120°–122°C., pK'a 8.5.

Analysis, Calc. for $C_{21}H_{27}NO \cdot HCl$: C, 72.92; H, 8.16; N, 4.05. Found: C, 72.87; H, 8.34; N, 4.04

EXAMPLE 33

N-Methyl-N-allyl-2-(3-phenoxyphenyl)propylamine hydrochloride, m.p. 135°–136°C., pK'a 7.6, was prepared generally by the method of Example 18.

Analysis, Calc. for $C_{19}H_{23}NO \cdot HCl$: C, 71.79; H, 7.61; N, 4.41. Found: C, 71.63; H, 7.80; N, 4.21.

EXAMPLE 34

A. 2-(3-Phenoxyphenyl)propylamine

One hundred grams of 2-(3-phenoxyphenyl)propionitrile, prepared according to Example 2D, 10 g. of Raney nickel, 250 ml. of ethyl alcohol, and 150 g. of ammonia were combined in a pressure vessel under an initial hydrogen pressure of 1000 p.s.i. The reaction was maintained under pressure, and heated at 70°–80°C., with shaking, for 4 hours, resulting in a 91 percent hydrogen uptake. After cooling and filtering the catalyst, the reaction mixture was poured into ice water, acidified with hydrochloric acid, washed with ethyl ether, basified with 10 percent sodium hydroxide, and extracted with ethyl ether. The ethyl ether layer was washed with water, dried over sodium sulfate, and evaporated to a residual oil, which was distilled to yield 78.9 g. of 2-(3-phenoxyphenyl)propylamine b.p., 158°–161°C./0.08 mm., $n_D^{25} = 1.5752$.

Analysis, Calc. for $C_{15}H_{17}NO$: C, 79.26; H, 7.54; N, 6.16. Found: C, 79.18; H, 7.29; N, 6.07.

B. 2-(3-Phenoxyphenyl)propylamine hydrochloride

Twenty grams of the above-prepared 2-(3-phenoxyphenyl)propylamine were dissolved in ethyl ether, and the resulting solution was saturated with hydrogen chloride gas, whereupon a solid precipitate formed. The precipitate was filtered, washed with ethyl ether, and dissolved in hot ethyl alcohol. Ethyl ether was added to turbidity, and the reaction mixture was cooled and scratched to yield 18.9 g. of 2-(3-phenoxyphenyl)-propylamine hydrochloride, m.p., 147°–147.5°C.

Analysis, Calc. for $C_{15}H_{17}NO \cdot HCl$: C, 68.30; H, 6.88; N, 5.31. Found: C, 68.11; H, 6.58; N, 5.32.

EXAMPLE 35

A. Ethyl 2-(3-phenoxyphenyl)propionate

Two hundred grams of 2-(3-phenoxyphenyl)propionic acid, prepared according to Example 2, were dissolved in 1500 ml. of ethanol, and hydrogen chloride gas was passed into the ethanolic solution until it was saturated. The reaction mixture was then refluxed with stirring overnight after which a large portion of the ethanol was evaporated in vacuo, and the remaining reaction mixture was poured into ice water. The reaction mixture was basified with 10 percent sodium hydroxide, and extracted twice with ethyl ether. The combined ether extracts were washed twice with water and dried over sodium sulfate. The ethyl ether was evaporated, leaving crude ethyl 2-(3-phenoxyphenyl)propionate as an oily residue. The preparation was repeated with an additional 200 g. of 2-(3-phenoxyphenyl)propionic acid. The crude residues were combined and distilled through a 15 cm. Vigreux column to yield 339.9 g. of ethyl 2-(3-phenoxyphenyl)propionate, b.p., 128°–134°C./0.15 mm., $n_D^{25} = 1.5458$.

Analysis, Calc. for $C_{17}H_{18}O_3$: C, 75.53; H, 6.71. Found: C, 75.75; H, 6.70.

B. 2-(3-Phenoxyphenyl)propanol

To 27.4 g. of lithium aluminum hydride in a flame dried, nitrogen-flushed flask was added approximately 1 liter of ethyl ether. The mixture was stirred vigorously for 45 minutes. Three hundred grams of ethyl 2-(3-phenoxyphenyl)propionate, prepared according to section A above, dissolved in 500 ml. of ethyl ether were then added dropwise to the lithium aluminum hydride suspension at such a rate that a gentle reflux was constantly maintained. After the ester addition was complete, the reaction mixture was stirred and refluxed gently overnight. After cooling the reaction to room temperature, decomposition was achieved by the cautious, dropwise addition of 44.5 ml. of water, 33.3 ml. of 20 percent sodium hydroxide and 155 ml. of water. A large amount of water was then added which formed an emulsion. This became clear when acidified. The reaction was then extracted with ethyl ether, the ether layer separated, and the aqueous layer extracted again with ethyl ether. The ether extracts were combined, washed with water, dried over sodium sulfate and a little sodium carbonate. The dried ether solution was then evaporated to an oily residue. This was distilled to yield 241.6 g. of 2-(3-phenoxyphenyl)propanol, b.p., 128°–131°C./0.1 mm., $n_D^{25} = 1.5771$.

Analysis, Calc. for $C_{15}H_{16}O_2$: C, 78.92; H, 7.06. Found: C, 78.65; H, 7.17.

EXAMPLE 36

2-(3-Phenoxyphenyl)propyl-N-methylcarbamate

To a solution of 2.51 g. of methyl isocyanate in 75 ml. of dry benzene was added dropwise with stirring at room temperature a solution of 10 g. of 2-(3-phenoxyphenyl)propanol, prepared according to Example 35, in 25 ml. of benzene, and the resulting reaction mixture was refluxed with stirring for 5 hours. The reaction mixture was then evaporated to an oil, and the oil distilled to yield 8.7 g. of 2-(3-phenoxyphenyl)propyl-N-methyl-carbamate, b.p., 170°–180°C./0.1 mm., $n_D^{25} = 1.5615$.

Analysis, Calc. for $C_{17}H_{19}NO_3$: C, 71.56; H, 6.71; N, 4.91. Found: C, 71.64; H, 6.90; N, 4.77.

EXAMPLE 37

2-(3-Phenoxyphenyl)propyl Acetate

Eleven and four-tenths g. of 2-(3-phenoxyphenyl)-propanol, prepared according to Example 35, 7 ml. of acetic anhydride, and approximately 100 ml. of pyridine were combined, and refluxed, with stirring, for 18 hours. Most of the pyridine was evaporated in vacuo, and the residue was dissolved in chloroform, washed with dilute hydrochloric acid, water, and dried over anhydrous sodium sulfate. The chloroform was removed by evaporation in vacuo and the resulting oily residue was distilled, yielding 10.6 g. of 2-(3-phenoxyphenyl)propyl acetate, b.p., 138°–145°C./0.1 mm., $n_D^{25}$ = 1.5478.

Analysis, Calc. for $C_{17}H_{18}O_3$: C, 75.53; H, 6.71. Found: C, 75.40; H, 6.59.

EXAMPLE 38

2-(3-Phenoxyphenyl)propyl propionate 2-(3-Phenoxyphenyl)propyl propionate was similarly prepared using appropriate starting materials, b.p., 142°–149°C./0.1 mm., $n_D^{25}$ = 1.5420.

Analysis, Calc. for $C_{18}H_{20}O_3$: C, 76.03; H, 7.09. Found: C, 75.73; H, 7.32.

EXAMPLE 39

2-(3-Phenoxyphenyl)propionohydroxamic acid

Sodium methoxide was prepared by the addition of 5 g. of sodium metal to 150 ml. of methanol. A solution of 7 g. of hydroxylamine hydrochloride dissolved in 100 ml. of methanol was then added to the cooled sodium methoxide solution, and the precipitated sodium chloride removed by filtration. Twenty-five and six-tenths grams of methyl 2-(3-phenoxyphenyl)propionate, prepared according to the method of Example 35, except that methanol was used in place of ethanol, were then added to the filtrate with stirring. The reaction mixture was stirred at room temperature for one-half hour and then refluxed, with stirring, for one and one-half hours. The reaction mixture was then cooled and acidified by the dropwise addition of 6N hydrochloric acid. After partial solvent removal in vacuo, a yellow oil formed, which subsequently crystallized. Recrystallization from a small amount of ethyl acetate and methylcyclohexane yielded 12.2 g. of 2-(3-phenoxyphenyl)propionohydroxamic acid, m.p., 121°–122°C.

Analysis, Calc. for $C_{15}H_{15}NO_3$: C, 70.02; H, 5.88; N, 5.44. Found: C, 69.95; H, 5.96; N, 5.41.

EXAMPLE 40

Various compounds within the scope of this invention were tested for anti-inflammatory activity in an erythema blocking assay which involved the following test procedure.

A modification of the Winder et al. (1958) method [Winder, C. V., Wax, J., Burr, V. and Posiere, C. E.: "A Study of Pharmacological Influences on Ultraviolet Erythema in Guinea Pigs", Arch. Int. Pharmacodyn., 116, 261, 1958] was used to measure anti-inflammatory activity of these compounds. Albino guinea pigs of either sex weighing 225-300 grams were shaved on the back and chemically (NAIR, Lotion Hair Remover, Carter Products, N. Y., N. Y.) depitated 18–20 hours before exposure to ultraviolet light. The animals were fasted overnight. Immediately after the guinea pigs were treated with a test compound, gummed notebook paper reinforcements were placed on their backs, and they were exposed to a high intensity ultraviolet light for 7 seconds. The ultraviolet light source was a Hanovia Lamp (Kromayer-Model 10) which was placed in contact with the skin of the guinea pig's back. After exposure, the reinforcements were removed and their backs wiped clean with a water soaked gauze sponge. The unexposed area under the reinforcements provided an area of contrast for grading the erythema. The animals were randomized and placed in clear plastic partitioned holders 10 × 20 cm. wide and 15 cm. high. Beginning 1 hour after exposure and thereafter at half-hour intervals for another 1½ hours, the degree of resulting erythema was graded by an arbitrary scoring system based upon the degree of contrast and redness formed. Anti-inflammatory agents delay the development of the erythema and therefore have their greatest effect at the initial grading periods. Therefore, the scores were weighed by a factor of 4, 3, 2, and 1 at the 1.0-, 1.5-, 2.0-, and 2.5-hour scoring times, respectively. The erythema was graded as follows:

| Score | Erythema Scoring System<br>Appearance of Exposed Area |
|---|---|
| 0 | No redness and no contrast |
| 1 | Slight redness with a faint reinforcement outline |
| 2 | Slight to moderate redness with a distinct outline |
| 3 | Marked redness with a distinct circular outline |

Total scores from each treatment group of five or six guinea pigs were compared to the control treatment and the percent inhibition calculated as follows:

$$100 \times \frac{\text{Control} - \text{Treatment}}{\text{Control}} = \text{Percent Inhibition}$$

Test compounds were prepared in a suspension of 1 percent methylcellulose in water and administered orally. Guinea pigs were treated orally with 1.0 cc./kg. of the suspensions. Control animals received 1.0 cc./kg. of a 1 percent methylcellulose suspension. The dose that produces a 50 percent inhibition of the erythemic response ($ED_{50}$) was calculated. The $ED_{50}$ results in (mg./kg.) are recorded in the following table:

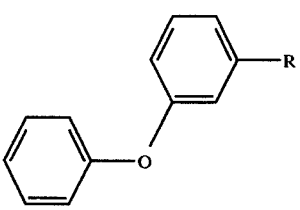

| R | Erythema Blocking Assay<br>Oral $ED_{50}$(mg. of compound/kg. of body wt.) |
|---|---|
| $CH_2CH_2NH_2 \cdot HCl$ | 75 |
| $CH_2CH_2NHCH_3 \cdot HCl$ | 10 |
| $CH_2CH_2N(CH_3)_2 \cdot HCl$ | 7 |
| CH—$CH_2NH_2 \cdot HCl$<br>\|<br>$CH_3$ | 1 |
| CH—$CH_2NHCH_3 \cdot HCl$<br>\|<br>$CH_3$ | 1 |

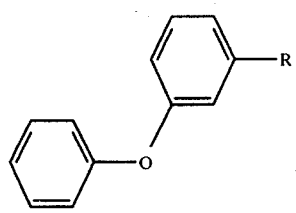

| R | Erythema Blocking Assay Oral ED$_{50}$(mg. of compound/kg. of body wt.) |
|---|---|
| CH—CH$_2$N(CH$_3$)$_2$.HCl<br>\|<br>CH$_3$ | 8 |
| CH—CH$_2$NH—CH⟨CH$_2$\|CH⟩.HCl<br>\|<br>CH$_3$ | 9 |
| CH—CH$_2$NHCH$_2$CH⟨CH$_2$\|CH$_2$⟩.HCl<br>\|<br>CH$_3$ | 20 |
| CH—CH$_2$—N⟨CH\|CH⟩⟨CH$_2$\|CH$_2$⟩.HCl<br>\|<br>CH$_3$ | 3 |
| CH—CH$_2$N⟨CH$_3$\|CH$_2$—CH⟨CH$_2$\|CH$_2$⟩⟩.HCl<br>\|<br>CH$_3$ | 3 |
| CH—CH$_2$NHCH$_2$CH=CH$_2$.HCl<br>\|<br>CH$_3$ | 10 |
| CHCH$_2$N⟨CH$_3$\|CH$_2$CH=CH$_2$⟩.HCl<br>\|<br>CH$_3$ | 3 |
| CHCH$_2$N⟨CH$_3$\|CH$_2$CH=C⟨CH$_3$\|CH$_3$⟩⟩.HCl<br>\|<br>CH$_3$ | 5 |
| CHCH$_2$NHCH$_2$CH$_2$φ.HCl<br>\|<br>CH$_3$ | 15 |
| CHCH$_2$N⟨CH$_3$\|CH$_2$CH$_2$φ⟩.HCl<br>\|<br>CH$_3$ | 5 |
| CHCH$_2$CH$_2$NH$_2$.HCl<br>\|<br>CH$_3$ | 2 |
| CH—CH$_2$CH$_2$NHCH$_3$.HCl<br>\|<br>CH$_3$ | 5 |
| CH—CH$_2$OH<br>\|<br>CH$_3$ | 2 |
| CH—CH$_2$—O—$\overset{O}{\overset{\|\|}{C}}$CH$_3$<br>\|<br>CH$_3$ | 8 |
| CH—CH$_2$O$\overset{O}{\overset{\|\|}{C}}$—CH$_2$CH$_3$<br>\|<br>CH$_3$ | 10 |

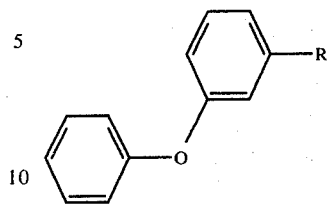

| R | Erythema Blocking Assay Oral ED$_{50}$(mg. of compound/kg. of body wt.) |
|---|---|
| CH—CH$_2$O$\overset{O}{\overset{\|\|}{C}}$—NHCH$_3$<br>\|<br>CH$_3$ | 40 |
| CH—$\overset{O}{\overset{\|\|}{C}}$—NH$_2$<br>\|<br>CH$_3$ | 3 |
| CH—$\overset{N=N}{\overset{\|\|}{C}}$⟨N\|NH⟩<br>\|<br>CH$_3$ | 10 |
| CH—$\overset{O}{\overset{\|\|}{C}}$—NHCH$_3$<br>\|<br>CH$_3$ | 30 |
| CH—$\overset{O}{\overset{\|\|}{C}}$—N⟨CH$_3$\|CH$_3$⟩<br>\|<br>CH$_3$ | 25 |
| CH—$\overset{O}{\overset{\|\|}{C}}$—NHOH<br>\|<br>CH$_3$ | 2 |
| CH—$\overset{O}{\overset{\|\|}{C}}$—NHCH$_2$COOH<br>\|<br>CH$_3$ | 5 |
| A.S.A. | 50 |

EXAMPLE 41

The inhibition of acetic acid-induced writhing in mice is used herein to demonstrate the relative analgesic activity of various compounds within the scope of this invention. A method similar to that reported by Koster, R., et al., "Acetic Acid for Analgesic Screening" Fed. Proc., 18:412(1959) was used to demonstrate the analgesic effects.

METHOD

Standard strain albino male mice, weighing 16–18 grams, were administered the treatments either subcutaneously or by gastric lavage. At various times after treatment, writhing was induced by the intraperitoneal administration of 60 mg./kg. of acetic acid (0.6 per cent). Each treatment group consisted of 6 mice. The total number of writhes for the treatment group were counted in a 10-minute observation period starting 5 minutes after the acetic acid administration. The treatment totals were compared to controls and a percent inhibition calculated as follows:

$$\text{Percent Inhibition} = 100 - \left(\frac{\text{Treatment total}}{\text{Control total}} \times 100\right)$$

The $ED_{50}$ values in the table which follows represents the doses in mg. of compound/kg. of body weight which will produce a 50 percent inhibition of the frequency of writhing.

| Test Compounds 2-(3-phenoxyphenyl)-R where R is | Analgesic Writhing Test Subcutaneous $ED_{50}$ mg./kg. |
|---|---|
| $CH_2CH_2NH_2 \cdot HCl$ | 4 |
| $CH_2CH_2NHCH_3 \cdot HCl$ | 25 |
| $CH_2CH_2N(CH_3)_2 \cdot HCl$ | 35 |
| $CHCH_2NH_2 \cdot HCl$ <br> \| <br> $CH_3$ | 20 |
| $CH-CH_2NHCH_3 \cdot HCl$ <br> \| <br> $CH_3$ | 20 |
| $CH-CH_2N(CH_3)_2 \cdot HCl$ <br> \| <br> $CH_3$ | 10 |
| $CH(4CH_2NHCH_3 \cdot HCl)$ <br> \| <br> $CH_2CH_3$ | 20 |
| $CH-CH_2-N-CH_2-CH(CH_2/CH_2) \cdot HCl$ <br> \|       \| <br> $CH_3$   $CH_3$ | <50 |
| A.S.A., (Aspirin, Lilly) | 20 |

The present invention includes within its scope pharmaceutical compositions comprising, as an active ingredient, at least one of the compounds of this invention in association with a pharmaceutical carrier or diluent. The compounds of this invention exhibit both oral and parenteral activity and can be formulated in dosage forms for oral, parenteral, rectal, or topical administration.

Solid dosage forms for oral administration include capsules, tablets, pills, powders, and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides inert diluents, such compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain in addition to the active substance, excipients such as cacoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 0.5 to 50 mg./kg. of body weight daily are administered to mammals to obtain effective relief of inflammation, pain, and fever.

The following examples further illustrate the pharmaceutical compositions which are a feature of this invention.

EXAMPLE 42

Tablets weighing 500 mg. and having the following compositions are prepared:

| | |
|---|---|
| 2-(3-phenoxyphenyl)propylamine hydrochloride | 250 mg. |
| starch | 190 mg. |
| colloidal silica | 50 mg. |
| magnesium stearate | 10 mg. |

EXAMPLE 43

Tablets weighing 200 mg. and having the following compositions are prepared:

| | |
|---|---|
| N-Methyl-2-(3-phenoxyphenyl)propylamine hydrochloride | 50 mg. |
| starch | 120 mg. |
| colloidal silica | 27 mg. |
| magnesium stearate | 3 mg. |

Tablets analogous to those described in Examples 49 and 50 can be prepared by replacing the above active ingredients by the same weight of any other compound coming within the scope of this invention. Such tablets can be enteric coated and can additionally comprise buffering agents and the like.

EXAMPLE 44

2-(3-phenoxyphenyl)propanol can be encapsulated in a soft gelatin film either neat or mixed with a suitable liquid diluent such as a vegetable oil. Other ingredients can be added if required for purposes such as improving dispersibility, promoting absorption, etc. Encapsulation can be accomplished by any suitable machine such as the Scherer rotary die machine described in "Remington's Pharmaceutical Sciences", 13th Ed., and well known in the art.

EXAMPLE 45

Suppository Formulation

| | |
|---|---|
| 2-(3-phenoxyphenyl)propylamine hydrochloride | 15.5% by wt. |
| White Wax, U.S.P. | 4.0% |
| Theobroma Oil, U.S.P. | 80.5% |

White wax and the 2-(3-phenoxyphenyl)propylamine hydrochloride are mixed with aid of gentle heat. Theobroma oil is shaved and added to the mixture slowly. After the theobroma oil has been completely melted, with the aid of additional heat as required, the mixture may be poured into suppository molds of suitable size for the desired dose; e.g., a 2.28 g. suppository of the above mixture yields a 400 mg. dose of 2-(3-phenoxyphenyl)propylamine hydrochloride.

EXAMPLE 46

Emulsion Formulation

| | |
|---|---|
| 2-(3-phenoxyphenyl)propionyl N-methyl carbamate | 1.33 g. |
| Soybean Oil | 26.7 g. |
| Span 60 | 2.27 g. |
| Tween 60 | 0.40 g. |
| Sucrose | 33.3 g. |
| Methylparaben | 0.1 g. |
| Propylparaben | 0.1 g. |
| Peppermint Oil | 0.05 g. |
| Water q.s. | 100. ml. |
| Dose: 15 ml., equivalent to 200 mg. of drug. | |

The Span 60 and soybean oil are mixed and heated to 70°C. Tween 60 and parabens are dispersed in approximately 100 ml. of water at 70°C. and sucrose is added. The oil phase is added to the aqueous phase in a suitable mixer such as a Waring Blender and mixed to produce a milky product. After cooling, the 2-(3-phenoxyphenyl)propionyl N-methylcarbamate and peppermint oil are added, and the mixture is agitated again.

Span 60 is sorbitan monostearate — Atlas Chemical Industries, Inc.

Tween 60 is polyoxyalkylene derivative of sorbitan monostearate — City Chemical Corp., N.Y., N.Y.

I claim:
1. A compound of the formula

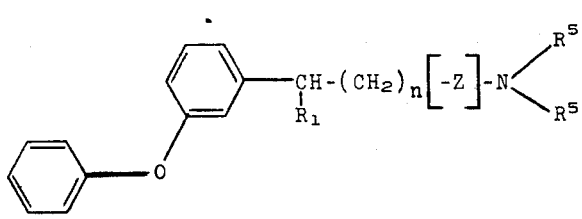

wherein $R_1$ is hydrogen, $C_1$ to $C_5$-alkyl, $C_2$ to $C_5$-alkenyl, $C_2$–$C_5$-alkynyl; $n$ is an integer of from 1 to 3; and each $R_5$ is the same or different and is hydrogen, $C_1$ to $C_5$-alkyl, $C_2$ to $C_6$-alkenyl, cyclopropyl, or cyclopropylmethyl, allyl, 3-methyl-2-butenyl, or phenethyl; and the pharmaceutically acceptable acid addition salts thereof.

2. A compound as defined in claim 1 wherein $R_1$ is $C_1$ to $C_5$-alkyl, $n$ is 1, and

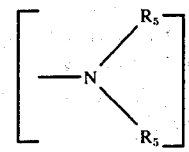

each $R_5$ is hydrogen, and the pharmaceutically acceptable acid addition salts thereof.

3. A compound as defined in claim 2 wherein the compound is 2-(3-phenoxyphenyl)propylamine hydrochloride.

4. A compound as defined in claim 1 wherein $R_1$ is $C_1$ to $C_5$-alkyl, $n$ is 1 and

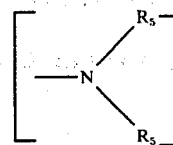

one $R_5$ is hydrogen and the other $R_5$ is $C_1$ to $C_5$-alkyl, and the pharmaceutically acceptable acid addition salts thereof.

5. A compound as defined in claim 4 wherein the compound is 2-(3-phenoxyphenyl)-N-methylpropyl amine hydrochloride.

6. A compound as defined in claim 1 wherein $R_1$ is hydrogen, $n$ is 1, and

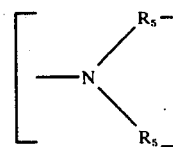

each $R_5$ is hydrogen, and the pharmaceutically acceptable acid addition salts thereof.

7. A compound as defined in claim 6 wherein the compound is 2-(3-phenoxyphenyl)ethylamine hydrochloride.

8. A compound as defined in claim 1 wherein $R_1$ is $C_1$ to $C_5$-alkyl, $n$ is 1, and

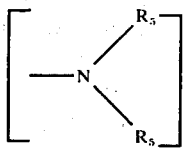

one $R_5$ is $C_1$ to $C_5$-alkyl and the other $R_5$ is $C_3$ to $C_6$-cycloalkyl, and the pharmaceutically acceptable acid addition salts thereof.

9. A compound as defined in claim 8 wherein the compound is 2-(3-phenoxyphenyl)-N-methyl-N-cyclopropyl-propylamine hydrochloride.

10. A compound as defined in claim 1 where $R_1$ is $C_1$ to $C_5$-alkyl, $n$ is 2, and

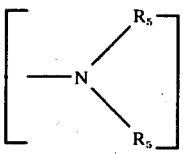

each $R_5$ is hydrogen, and the pharmaceutically acceptable acid addition salts thereof.

11. A compound as defined in claim 10 wherein the compound is 3-(3-phenoxyphenyl)butylamine hydrochloride.

12. A compound as defined in to $C_1$ wherein $R_1$ is $C_1$ $C_5$-alkyl, $n$ is 1, and

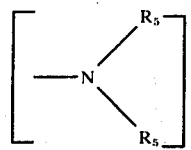

one $R_5$ is $C_1$ to $C_5$-alkyl and the other $R_5$ is $C_2$ to $C_6$-alkenyl, and the pharmaceutically acceptable salts thereof.

13. A compound as defined in claim 12 wherein the compound is 2-(3-phenoxyphenyl)-N-allyl-N-methyl-propylamine hydrochloride.

14. A compound as defined in claim 12 wherein the compound is 2-(3-phenoxyphenyl)-N-methyl-N-(3-methyl-2-butenyl)propylamine hydrochloride.

15. A compound as defined in claim 1 wherein $R_1$ is $C_1$ to $C_5$-alkyl, $n$ is 1, and

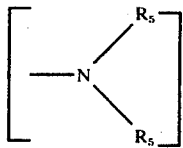

one $R_5$ is hydrogen and the other $R_5$ is $C_3$ to $C_6$-cycloalkyl, and pharmaceutically acceptable salts thereof.

16. A compound as defined in claim 15 wherein the compound is 2-(3-phenoxyphenyl)-N-cyclopropyl-propylamine hydrochloride.

* * * * *

UNITED STATES PATENT AND TRADEMARK OFFICE
CERTIFICATE OF CORRECTION

PATENT NO. : 3,972,934
DATED : August 3, 1976
INVENTOR(S) : Winston S. Marshall

It is certified that error appears in the above-identified patent and that said Letters Patent are hereby corrected as shown below:

Column 12, line 19, "6NHCl" should be -- 6N HCl --.

Column 14, about line 16, "pripiona-" should be -- propiona- --.

Column 21, about line 19, 
$$--\underset{\underset{CH}{\diagdown}}{\overset{\diagup CH_2}{CH|}}--\quad \text{should be} \quad --\underset{\underset{CH_2}{\diagdown}}{\overset{\diagup CH_2}{CH|}}--;\text{ and}$$

and about line 25, 
$$--N\underset{CH\diagleft}{\overset{\diagup CH}{\diagdown}} \quad \text{should be} \quad --N\underset{CH\diagleft}{\overset{\diagup CH_3}{\diagdown}} --.$$

Column 23, under the column, "Test Compounds...", about line 30, in 
$$CH\overset{4CH_2NHCH_3 \cdot HCl}{\diagup}\quad \text{delete "4".}$$

Column 24, about line 17, "cacoa" should be --cocoa--; and also about line 61 insert a comma between "film" and "either".

Column 25, in the structural formula in Claim 1, delete "[-Z]".

Column 26, about line 4, delete the period between "each" and "$R_5$"; in Claim 2, delete the structure in brackets; in Claim 4, delete the structure in brackets; and in Claim 6, delete the structure in brackets.

Column 27, in Claim 8, delete the structure in brackets; in Claim 10, delete the structure in brackets; and in Claim 12, line 34, "to $C_1$" should be --Claim 1--; and also on that same line, insert the word --to-- between "$C_1$" and "$C_5$-".

UNITED STATES PATENT AND TRADEMARK OFFICE
CERTIFICATE OF CORRECTION

PATENT NO. : 3,972,934

DATED : August 3, 1976

INVENTOR(S) : Winston D. Marshall

It is certified that error appears in the above-identified patent and that said Letters Patent is hereby corrected as shown below:

Column 28, in Claim 12, delete the structure in brackets; and in Claim 15, delete the structure in brackets.

Signed and Sealed this

Fourth Day of October 1983

[SEAL]

Attest:

Attesting Officer

GERALD J. MOSSINGHOFF

Commissioner of Patents and Trademarks